(12) United States Patent
Chbat et al.

(10) Patent No.: US 10,842,411 B2
(45) Date of Patent: Nov. 24, 2020

(54) NON-INVASIVE ESTIMATION OF INTRA-PLEURAL PRESSURE AND/OR COMPUTATION OF WORK OF BREATHING BASED ON A NON-INVASIVE ESTIMATION OF INTRA-PLEURAL PRESSURE

(71) Applicant: KONINKLIJKE PHILIPS N.V., Eindhoven (NL)

(72) Inventors: Nicolas Wadih Chbat, White Plains, NY (US); Antonio Albanese, New York, NY (US); Syed Waseem Haider, Somers, NY (US); Nikolaos Karamolegkos, New York, NY (US); Adam Jacob Seiver, Los Altos Hills, NY (US)

(73) Assignee: Koninklijke Philips N.V., Eindhoven (NL)

( * ) Notice: Subject to any disclaimer, the term of this patent is extended or adjusted under 35 U.S.C. 154(b) by 631 days.

(21) Appl. No.: 14/901,115

(22) PCT Filed: Jun. 19, 2014

(86) PCT No.: PCT/IB2014/062406
§ 371 (c)(1),
(2) Date: Dec. 28, 2015

(87) PCT Pub. No.: WO2014/207623
PCT Pub. Date: Dec. 31, 2014

(65) Prior Publication Data
US 2016/0135713 A1 May 19, 2016

Related U.S. Application Data

(60) Provisional application No. 61/840,658, filed on Jun. 28, 2013.

(30) Foreign Application Priority Data

Aug. 2, 2013 (EP) .................................. 13179067

(51) Int. Cl.
*A61B 5/087* (2006.01)
*A61B 5/085* (2006.01)
(Continued)

(52) U.S. Cl.
CPC .............. *A61B 5/085* (2013.01); *A61B 5/037* (2013.01); *A61B 5/038* (2013.01); *A61B 5/087* (2013.01);
(Continued)

(58) Field of Classification Search
CPC ............ A61B 5/08; A61B 5/085; A61B 5/087
See application file for complete search history.

(56) References Cited

U.S. PATENT DOCUMENTS 4,597,394 A * 7/1986 Sackner ................ A61B 5/1135
600/590
4,856,532 A * 8/1989 Johnson ................. A61B 5/085
600/533
(Continued)

FOREIGN PATENT DOCUMENTS

EP 0078677 A2 5/1983
JP S5886142 A 5/1983
(Continued)

OTHER PUBLICATIONS

Albanese et al: "Real-Time Noninvasive Estimation of Intrapleural Pressure in Mechanically Ventilated Patients: A Feasibility Study"; IEEE 35th Annual International Conference of the IEEE EMBS, pp. 5211-5215.
(Continued)

*Primary Examiner* — Puya Agahi
(74) *Attorney, Agent, or Firm* — Daniel H. Brean

(57) ABSTRACT

A method includes obtaining a first physiological parameter indicative of a non-invasively measured airway pressure of a subject, obtaining a second physiological parameter indicative of a non-invasively measured air flow into the lungs of the subject, and estimating a third physiological parameter indicative of an intra-pleural pressure of the subject based on the first and second physiological parameters and generating a signal indicative thereof. An other method includes obtaining a first physiological parameter indicative of a non-invasively estimated intra-pleural pressure of a subject, determining a second physiological parameter indicative of a lung volume of the subject that is based on a third physiological parameter indicative of a non-invasively measured air flow into the lungs of the subject, and determining a work of breathing based on the first and second physiological parameters and generating a signal indicative thereof.

22 Claims, 10 Drawing Sheets

(51) Int. Cl.
  A61M 16/00   (2006.01)
  A61B 5/03    (2006.01)
  A61B 5/091   (2006.01)
  A61B 5/00    (2006.01)

(52) U.S. Cl.
  CPC ............ *A61B 5/091* (2013.01); *A61B 5/4836* (2013.01); *A61B 5/7278* (2013.01); *A61M 16/00* (2013.01); *A61M 16/026* (2017.08); *A61B 2562/0247* (2013.01); *A61M 2016/0027* (2013.01); *A61M 2016/0033* (2013.01); *A61M 2210/105* (2013.01); *A61M 2230/46* (2013.01); *A61M 2230/65* (2013.01)

(56) References Cited

U.S. PATENT DOCUMENTS

| | | | | |
|---|---|---|---|---|
| 4,860,766 | A * | 8/1989 | Sackner | A61B 5/113 600/561 |
| 5,316,009 | A | 5/1994 | Yamada | |
| 5,316,010 | A * | 5/1994 | Brown | A61B 5/085 600/533 |
| 7,588,453 | B2 | 9/2009 | Ma | |
| 2004/0040560 | A1* | 3/2004 | Euliano | A61B 5/08 128/204.23 |
| 2009/0062674 | A1* | 3/2009 | Jin | A61B 5/087 600/529 |
| 2012/0103334 | A1* | 5/2012 | Sinderby | A61B 5/08 128/204.18 |
| 2013/0109990 | A1* | 5/2013 | Akingba | A61B 5/03 600/529 |
| 2016/0135713 | A1 | 5/2016 | Chbat et al. | |

FOREIGN PATENT DOCUMENTS

| | | |
|---|---|---|
| JP | 2010142594 A | 7/2010 |
| RU | 2207159 C2 | 6/2003 |

OTHER PUBLICATIONS

Al-Rawas et al: "Inaccurate Work of Breathing Data Displayed on Ventilator During Proportional Assist Ventilation"; p. 111, 2009.
Avanzolini et al: "Real-Time Tracking of Parameters of Lung Mechanics: Emphasis on Algorithm Tuning"; J. Biomed. Eng. 1990. vol. 12, Nov. 1990, pp. 489-495.
Avanzolini et al: "Influence of Flow Pattern on the Parameter Estimates of a Simple Breathing Mechancis Model"; IEEE Transactions on Biomedical Engineereing, vol. 42, No. 4, Apr. 1995.
Avanzolini et al: "A New Approach for Tracking Respiratory Mechanical Parameters in Real-Time"; Annals of Biomedial Engineering, vol. 25, pp. 154-163, 1997.
Banner et al: "Partially and Totally Unloading Respiratory Muscles Based on Real-Time Measurements of Work of Breathing"; Chest, vol. 106, No. 6, pp. 1835-1842, Dec. 1994.
Banner et al: "Power of Breathing Determined Noninvasively With Use of an Artificial Network in Patients With Respiratory Failure"; Crit Care Med, vol. 34, No. 4, pp. 1052-1059, 2006.
Benditt: "Esophageal and Gastric Pressure Measurements"; Respiratory Care, Jan. 2005, vol. 50, No. 1, pp. 68-75.
Blanch et al: "A New Respiratory Monitor That Enables Accurate Measurement of Work of Breathing: A Validation Study"; Respiratory Care, Sep. 1994, vol. 39, No. 9, pp. 897-905.
Fernando: "The Work of Breathing of Mechanically Ventilated Patients"; IEEE/EMBS Proceedings of the 19th International Conference, 1997, Chicago, Illinois, pp. 255-258.
Lauzon et al: "Estimation of Time-Varying Respiratory Mechanical Parameters by Recursive Least Squares"; J. Appl Physiol. vol. 71, No. 3, pp. 1159-1165.
Vahidi et al: "Recursive Least Squares With Forgetting for Online Estimation of Vehicle Mass and Road Grade:Theory and Experiments"; Vehichal System Dynamics, vol. 43, No. 1, pp. 31-55, 2005.
Younes et al:"A Method for Measuring Passive Elastance During Proportional Assist Ventilation"; Am J Respir Crit Care Med, vol. 164, pp. 50-60, 2001.
Maquet Getinge Group, Ventilation Servo-I With Nava Freeing the Full Potential of Synchrony Brochure, 2012, pp. 1-10.
Carefusion, Avea Ventilator Brochure, 2013, p. 1-4.
Magder S.A. et al., "Effects of negative pleural pressure on left ventricular hemodynamics", American Journal of Cariology, Cahners Publishing Co., Newton, MA, vol. 52, No. 5, (Sep. 1, 1983), pp. 588-593.
Jackson, A.C. et al., "Digital computer simulation of respiratory mechanics", Computers and Biomedical Research, Academic Press, London, GB. vol. 6, No. 1, (Feb. 1, 1973), pp. 27-56.
Moller, K. et al., "Hierarchical modeling for medical decision support", Biomedical Engineering and Informatics (BMEI), 2011 4th International COnference on IEEE, (Oct. 15, 2011), pp. 960-964.

* cited by examiner

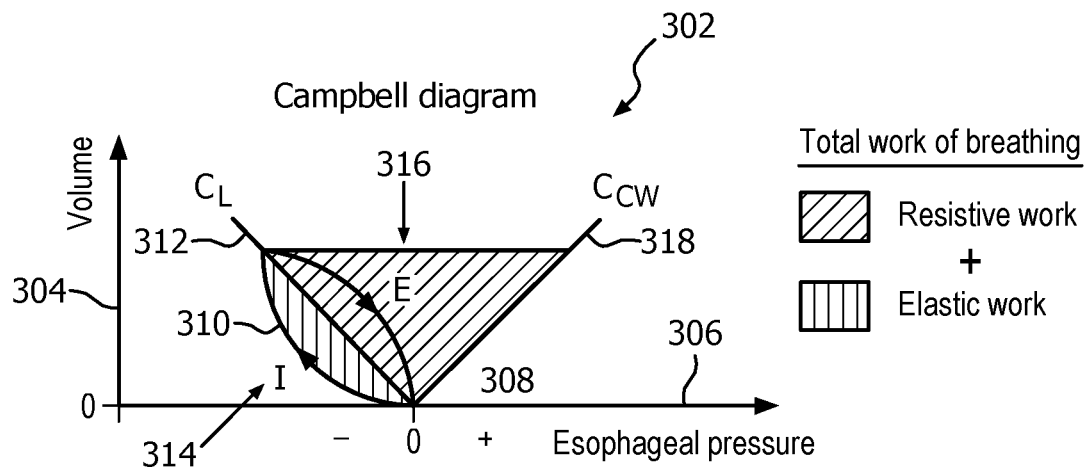
FIG. 3
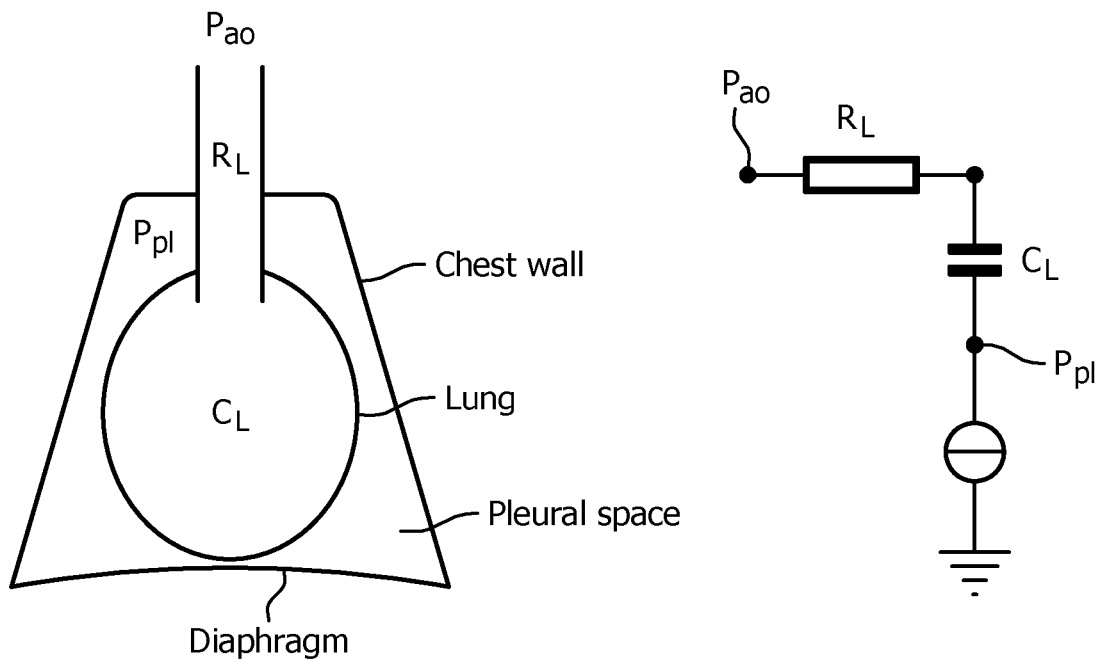
FIG. 4
FIG. 5

NON-INVASIVE ESTIMATION OF INTRA-PLEURAL PRESSURE AND/OR COMPUTATION OF WORK OF BREATHING BASED ON A NON-INVASIVE ESTIMATION OF INTRA-PLEURAL PRESSURE

CROSS-REFERENCE TO PRIOR APPLICATIONS

This application is the U.S. National Phase application under 35 U.S.C. § 371 of International Application No. PCT/IB2014/062406, filed on Jun. 19, 2014, which claims the benefit of U.S. Provisional Patent Application No. 61/840,658, filed on Jun. 28, 2013 and European Patent Application No. 13179067.7, filed on Aug. 2, 2013. These applications are hereby incorporated by reference herein.

The following generally relates to determining a physiological state of a subject and more particularly to estimating an intra-pleural pressure of the subject based on non-invasively determined parameters and/or computing a work of breathing metric of the subject based on a non-invasively estimated intra-pleural pressure of the subject.

Work of Breathing (WOB) is defined as the effort done by the respiratory muscles in order to breath. When a patient is connected to a mechanical ventilator, the WOB can be divided into two components: 1) the physiologic work of breathing, which is dissipated against the resistive and elastic pressures of the respiratory system, and 2) the imposed work of breathing due to the breathing apparatus (endotracheal tube and ventilator). The total WOB has been computed at each breath and normalized with respect to tidal volume to give Joule/L.

Real-time measurements of WOB in mechanically ventilated patients can be used to assess patient readiness for weaning, to appropriately select pressure support ventilation levels, to diagnose and treat excessive respiratory muscle loading and to monitor and prevent respiratory muscle fatigue or atrophy. The gold standard for WOB computation is the Campbell diagram, which is constructed by plotting lung volume against intra-pleural pressure, forming the pressure-volume loop. The area enclosed within the inspiratory portion of the pressure-volume loop and the chest wall compliance line indicates the WOB.

The Campbell diagram is an effective tool to evaluate the effects of lung mechanics abnormalities on WOB and it allows partitioning of WOB into its flow-resistive component (both physiologic and imposed) and elastic component. Unfortunately, direct measurement of intra-pleural pressure is a significantly invasive procedure. To construct the Campbell diagram, esophageal pressure has been used as a surrogate variable of intra-pleural pressure.

Unfortunately, measuring the esophageal pressure is not a trivial task and it requires expert operators for the correct placement and inflation of the balloon, special equipment, and particular attention to avoid errors and artifacts, mostly due to patient coughing, swallowing and cardiogenic effects. As a consequence, daily monitoring of WOB via the Campbell diagram has not been accepted at the bedside as a routine clinical practice and the popularity of commercial devices utilized this diagram has progressively declined.

Aspects described herein address the above-referenced problems and others.

The following describes an approach to non-invasively determining intra-pleural pressure and/or one or more other parameters. In addition, the following describes an approach to determining a Work of Breathing (WOB) value based on a non-invasively determined intra-pleural pressure.

In one aspect, a method includes obtaining a first physiological parameter indicative of a non-invasively measured airway pressure of a subject, obtaining a second physiological parameter indicative of a non-invasively measured air flow into the lungs of the subject, and estimating a third physiological parameter indicative of an intra-pleural pressure of the subject based on the first and second physiological parameters and generating a signal indicative thereof.

In another aspect, a method includes obtaining a first physiological parameter indicative of a non-invasively estimated intra-pleural pressure of a subject, determining a second physiological parameter indicative of a lung volume of the subject that is based on a third physiological parameter indicative of a non-invasively measured air flow into the lungs of the subject, and determining a work of breathing based on the first and second physiological parameters and generating a signal indicative thereof.

In another aspect, a physiological parameter determining apparatus includes a parameter estimator that estimates an intra-pleural pressure of a subject based on a non-invasively measured airway pressure of a subject and a non-invasively measured air flow into the lungs of the subject by fitting a mechanics model of the lungs to the non-invasively measured airway pressure and the non-invasively measured air flow into the lungs and minimizing a sum of squared residuals between the non-invasively measured airway pressure and a predicted airway pressure. The physiological parameter determining apparatus further includes a metric determiner that determines a Campbell diagram based on the estimated intra-pleural pressure and a lung volume determined from the air flow into the lungs, and determines a work of breathing for the subject based on an area within a pressure-volume loop and a chest wall compliance line of the Campbell diagram.

The invention may take form in various components and arrangements of components, and in various steps and arrangements of steps. The drawings are only for purposes of illustrating the preferred embodiments and are not to be construed as limiting the invention.

FIG. 1 schematically illustrates a physiological parameter determining apparatus in connection with a ventilator.

FIG. 2 schematically illustrates an example of the physiological parameter determining apparatus, including a parameter estimator and a metric determiner.

FIG. 3 shows an example Campbell diagram generated using the non-invasively determined intra-pleural pressure.

FIG. 4 illustrates a mechanical model used to non-invasively estimate the intra-pleural pressure.

FIG. 5 illustrates an electrical model, equivalent to the mechanical model of FIG. 5, used to non-invasively estimate the intra-pleural pressure.

Figure 2:
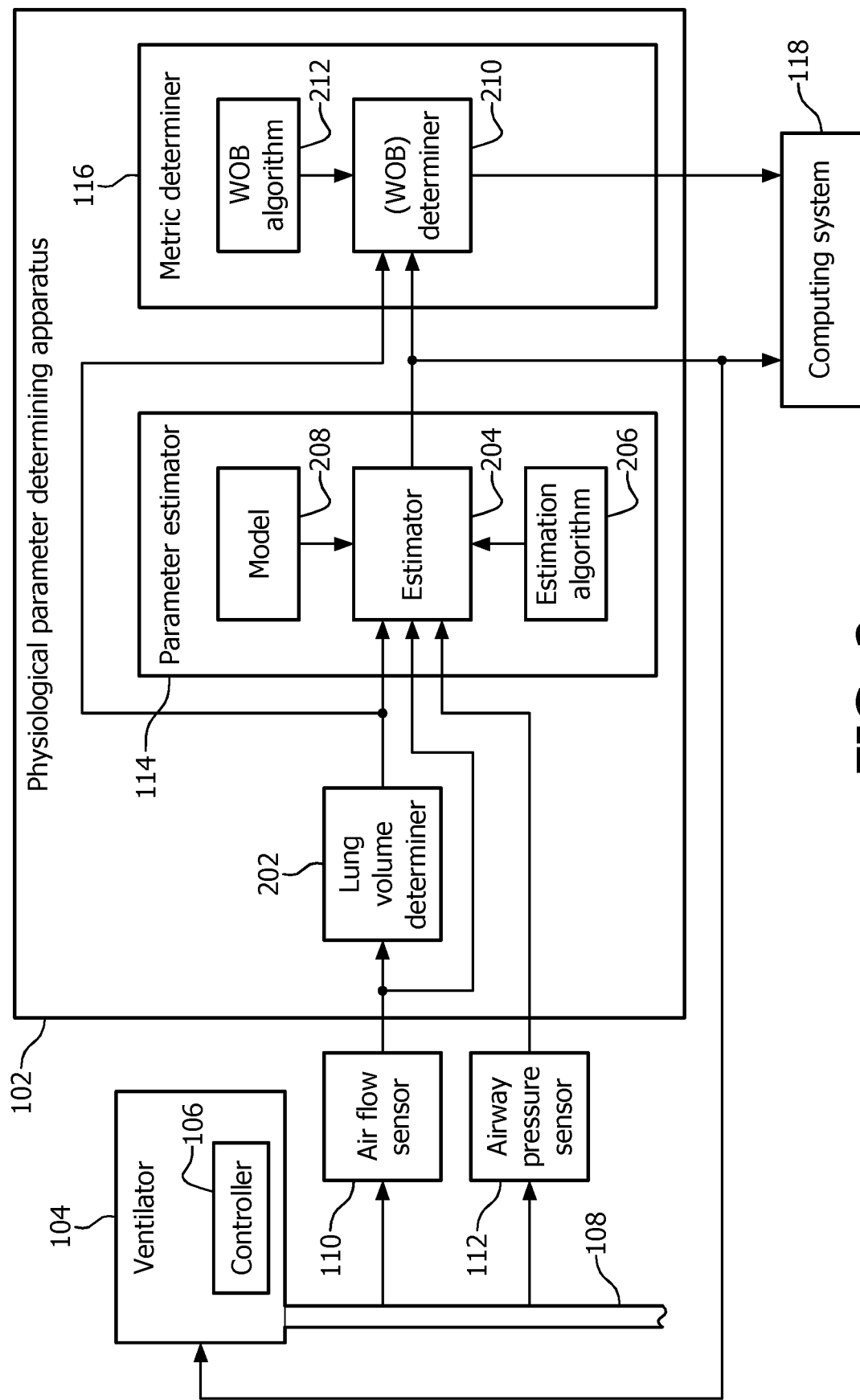
Figure 6:
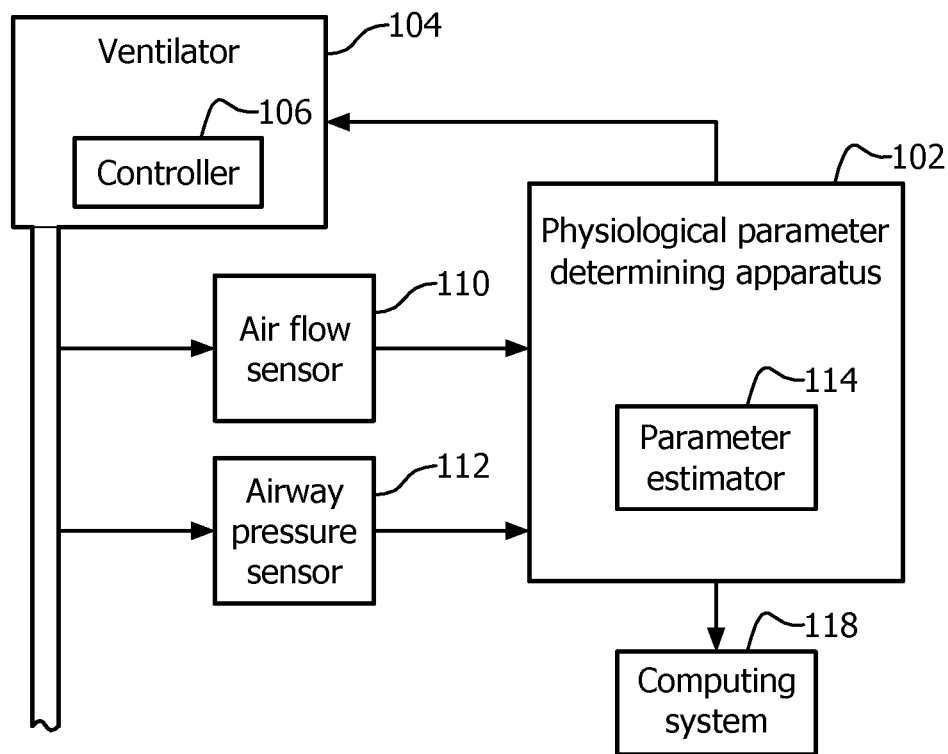

FIG. 6 schematically illustrates a variation of the physiological parameter determining apparatus of FIG. 2 without the metric determiner.

Figure 7:
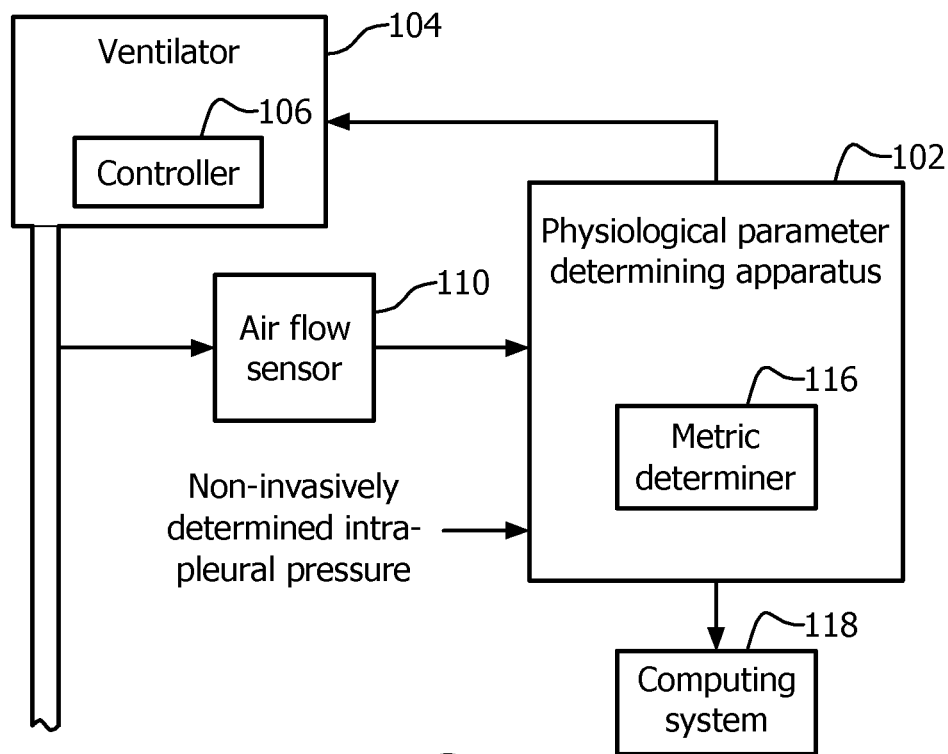

FIG. 7 schematically illustrates a variation of the physiological parameter determining apparatus of FIG. 2 without the parameter estimator.

Figure 8:
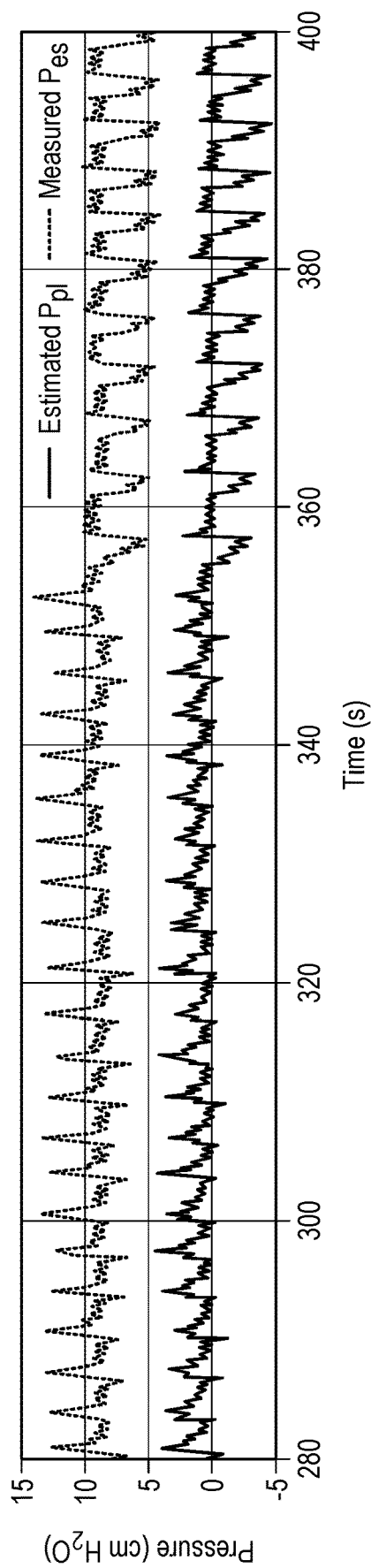

FIG. 8 illustrates a plot of a non-invasive estimated intra-pleural pressure, estimated as described herein, and a measured esophageal pressure.

Figure 9:
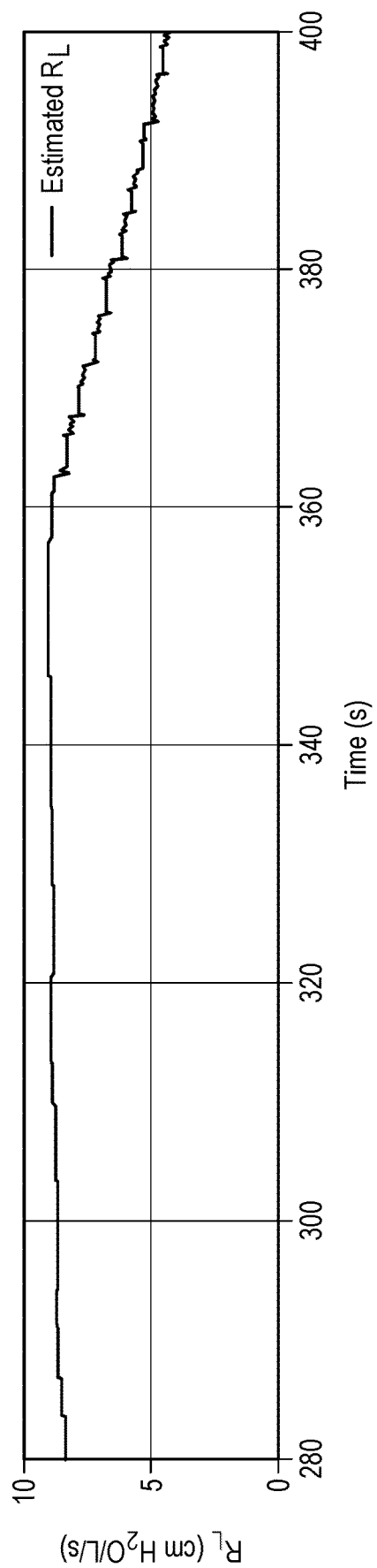

FIG. 9 illustrates a plot of an estimated lung resistance, estimated as described herein.

Figure 10:
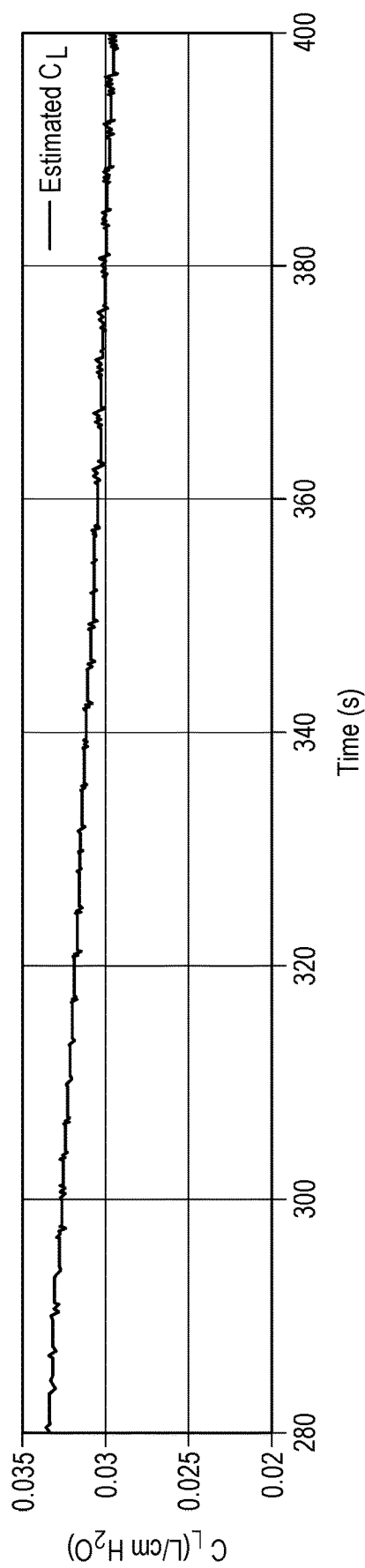

FIG. 10 illustrates a plot of an estimated lung compliance, estimated as described herein.

Figure 11:
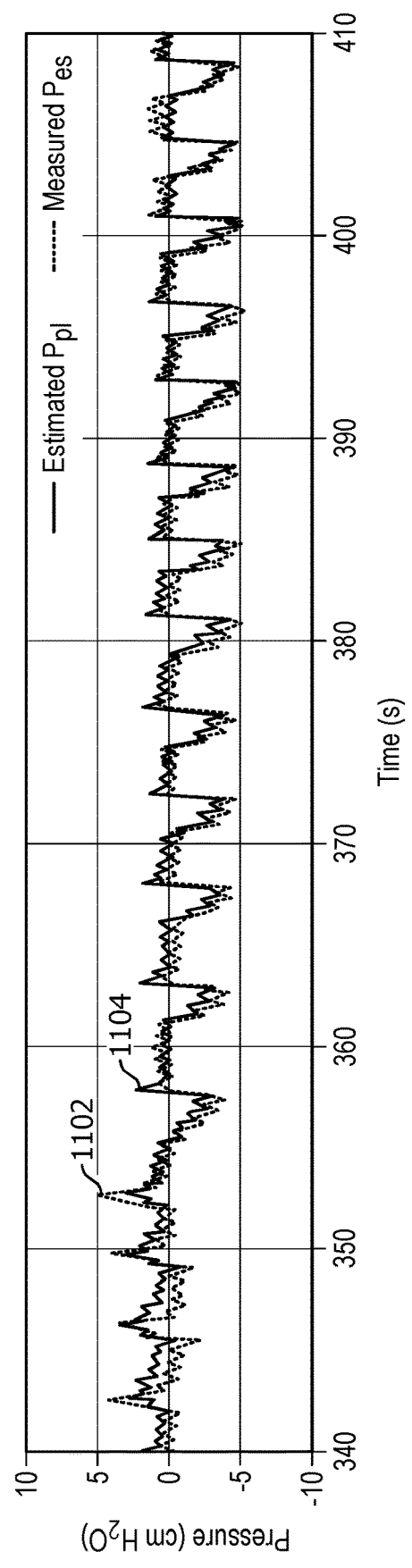

FIG. 11 shows a corrected measured esophageal pressure and the non-invasive estimated intra-pleural pressure.

Figure 12:
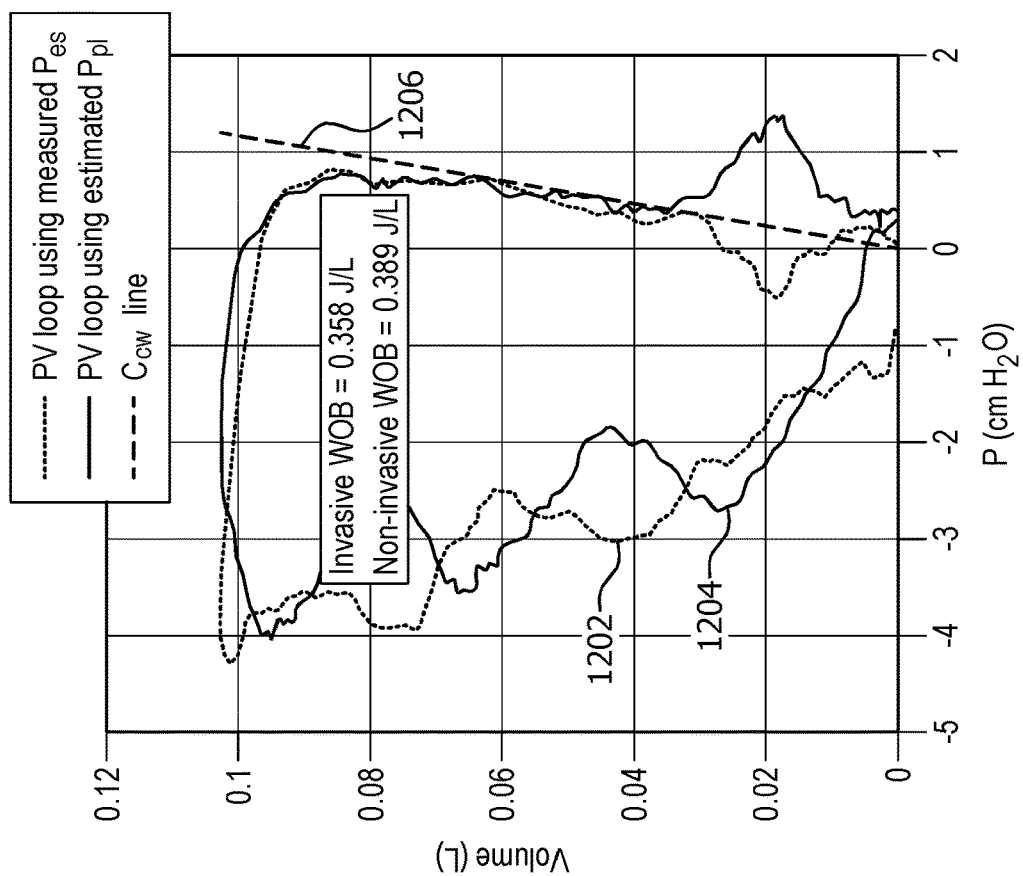

FIG. 12 illustrates the pressure-volume loop based on the non-invasively estimated intra-pleural pressure in connection with the pressure-volume loop based on the measured esophageal pressure.

Figure 13:
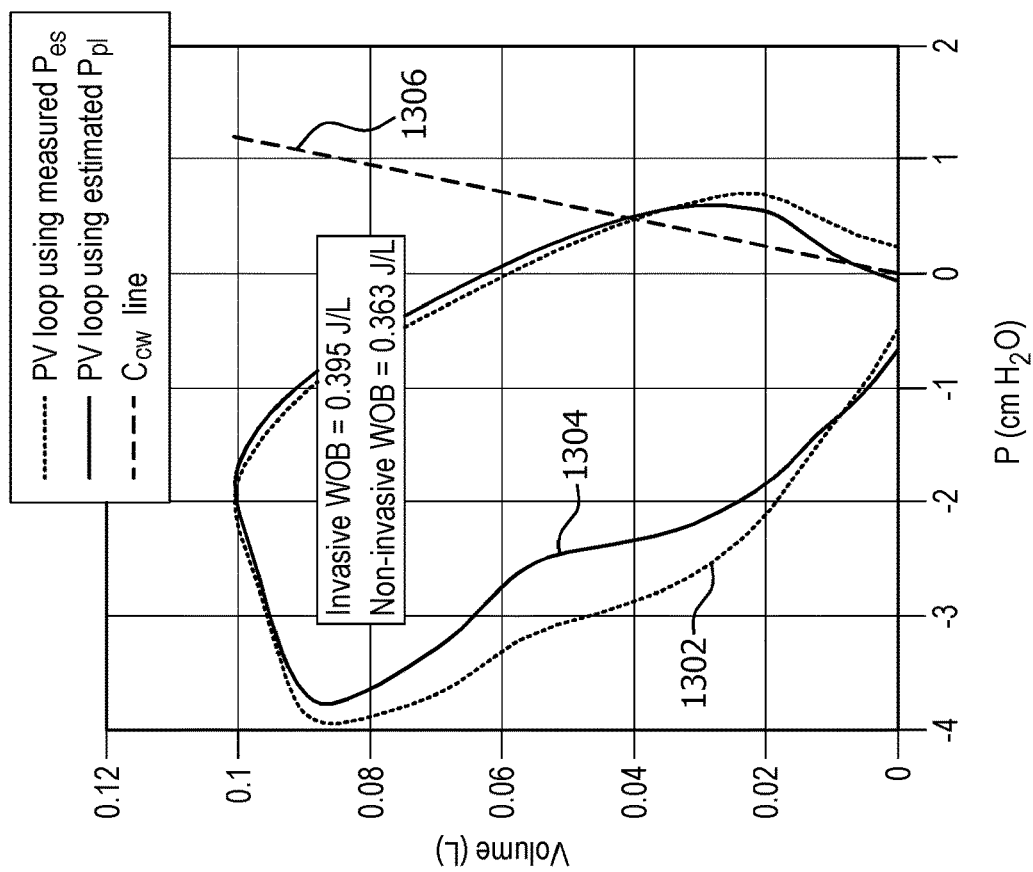

FIG. 13 illustrates the pressure-volume loop based on the non-invasively estimated intra-pleural pressure in connection with the pressure-volume loop based on the measured esophageal pressure after low-pass filtering to remove cardiogenic components.

Figure 14:
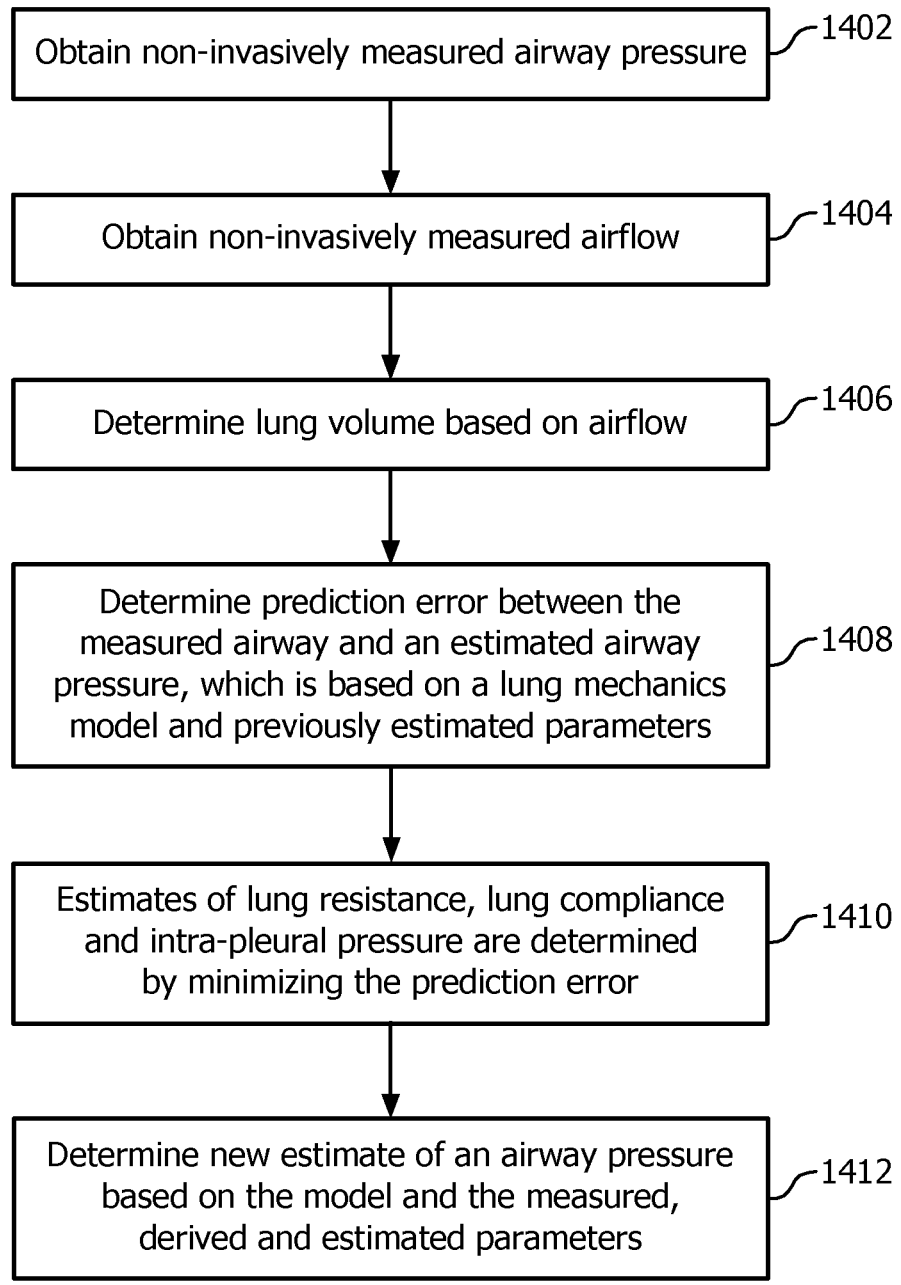

FIG. 14 illustrates an example method for estimating intra-pleural pressure based on non-invasively determined parameters.

Figure 15:
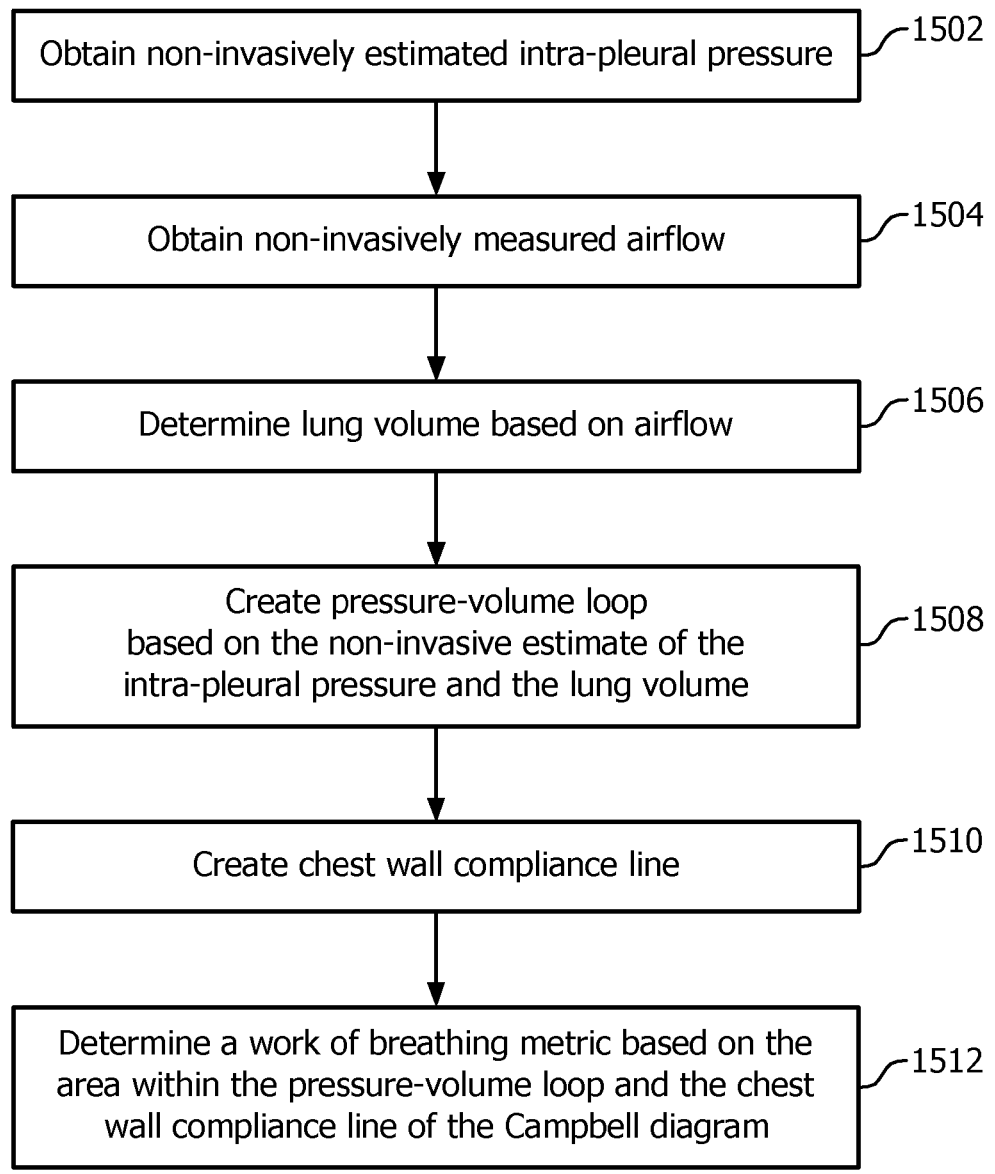

FIG. 15 illustrates an example method for determining a work of breathing metric based on a non-invasively determined intra-pleural pressure.

Figure 16:
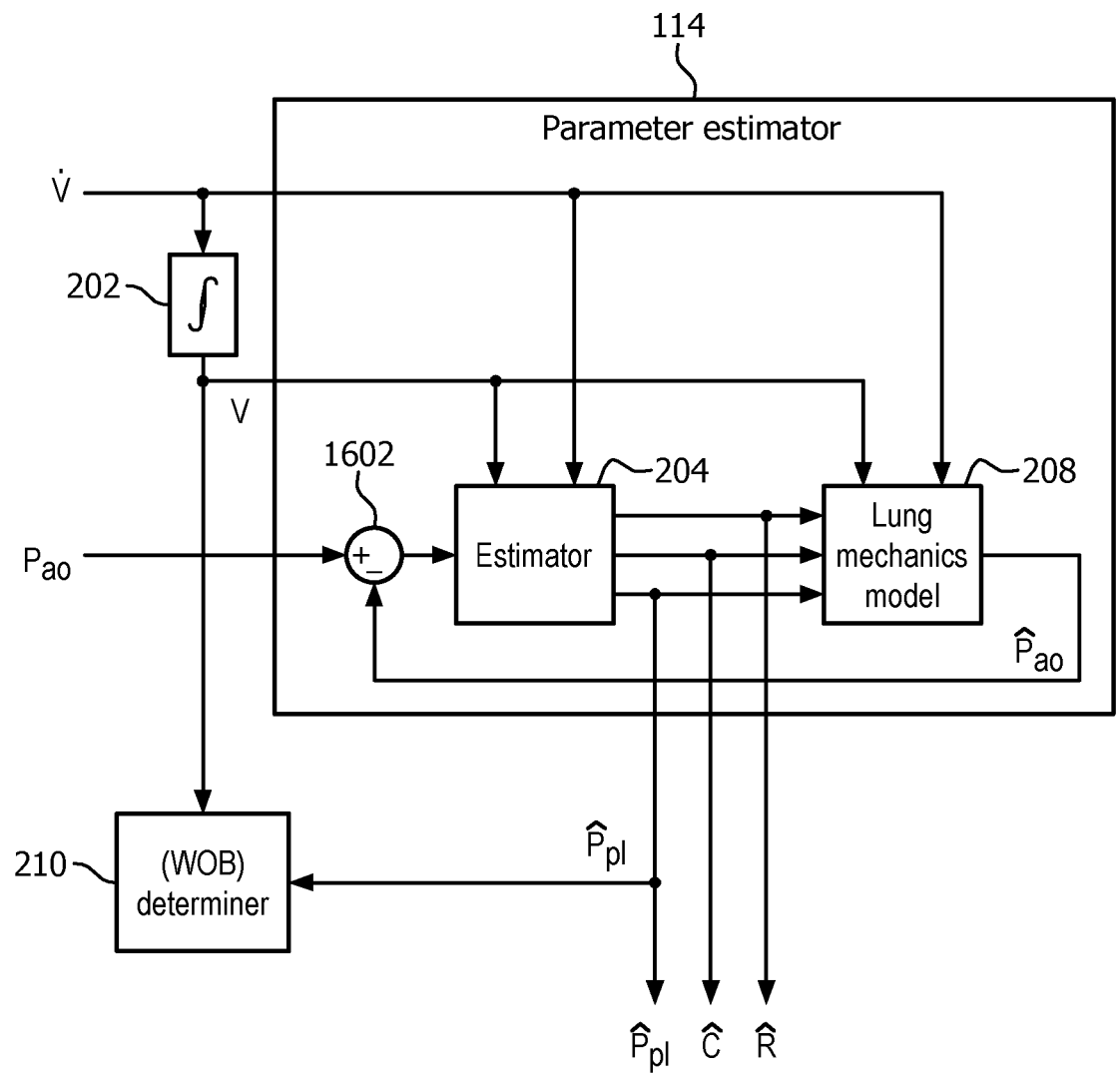

FIG. 16 schematically illustrates an example of the parameter estimator in connection with an RLS algorithm.

The following describes an approach to non-invasively determined intra-pleural pressure and/or utilized the non-invasively determined intra-pleural pressure and/or other non-invasively determined intra-pleural pressure to determine a Work of Breathing (WOB) metric for a subject.

Figure 1:
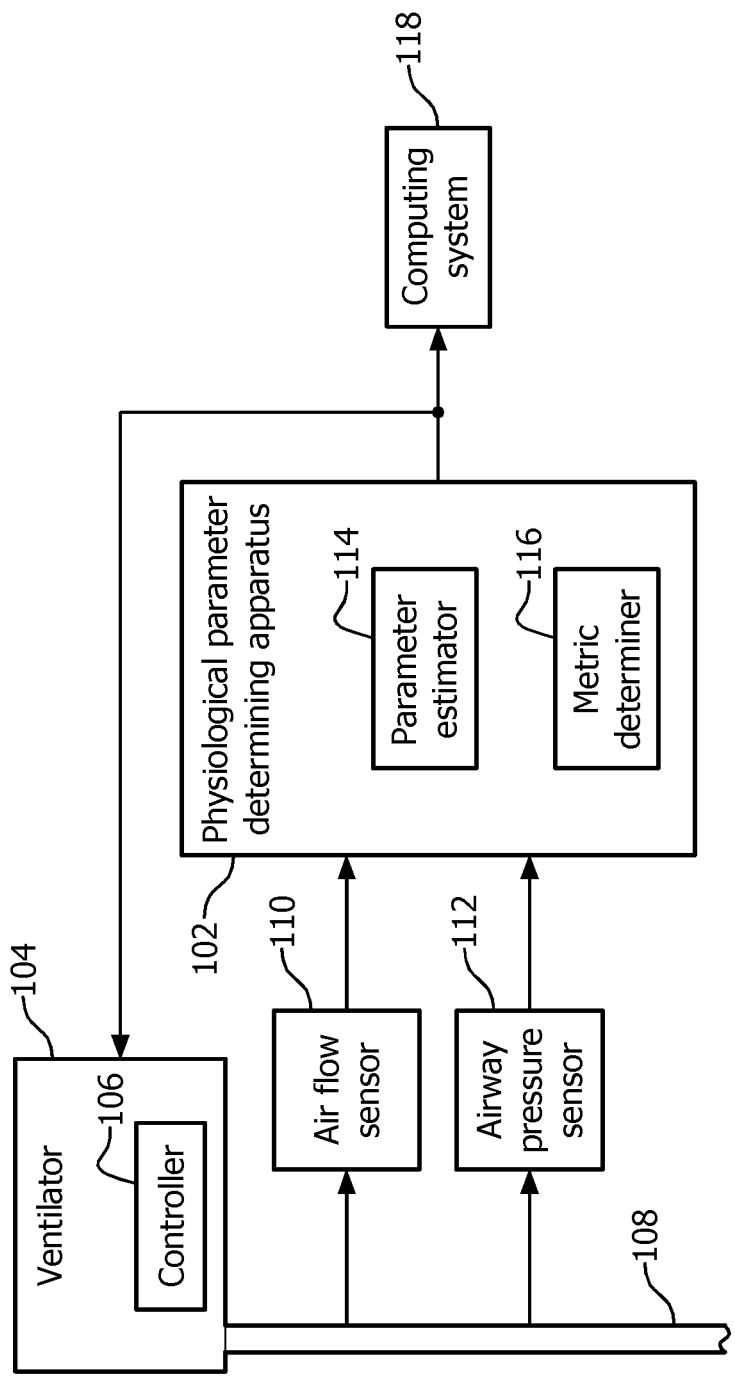

FIG. 1 illustrates a physiological parameter determining apparatus 102 in connection with a ventilator 104, which can be used alternatively in connection with invasive and non-invasive applications. A controller 106 controls the ventilator 104.

In the illustrated embodiment, a device 108 provides an air path from the ventilator 104 to a subject or object. In the case of invasive ventilation, the device 108 can be an endotracheal tube, a tracheostomy tube, or the like, including a 'Y' junction. In the case of non-invasive, the device 108 can be a nasal mask, a full face mask, or the like, including any tubing between the ventilator 104 and the mask.

An airway pressure sensor 112 measures a pressure at the airway, and an air flow sensor 110 measures an air flow at the airway. In the case of invasive ventilation, the sensors 110 and 112 can be connected to the 'Y' junction or other portion of the device 108. In the case of non-invasive ventilation, the sensors 110 and 112 can be connected to the patient mask or other portion of the device 108.

The physiological parameter determining apparatus 102 receives, as an input, the measured air flow and the measured airway pressure, and includes at least one of a parameter estimator 114 and/or a metric determiner 116, which process the received data and/or data derived therefrom, such as a parameter and/or metric indicative of a physiological and/or heath state of a subject.

The parameter estimator 114 processes the input measured air flow and airway pressure and determines one or more parameters based thereon. As described in greater detail below, the parameter estimator 114 at least estimates an intra-pleural pressure based by processing the input measured air flow and airway pressure. Other parameters include, but are not limited to, lung resistance and lung compliance. The estimated intra-pleural pressure may be fed back to a control loop of the ventilator controller 106 to facilitate control of the ventilator 104, a computing system 118, which assesses respiratory health based thereon and/or otherwise process the data, and/or otherwise utilized.

The metric determiner 116 processes the input measured air flow and at least one estimated parameter output by the parameter estimator 114 and generates a physiological metric based thereon. As described in greater detail below, the metric determiner 116 at least determines a WOB for a subject by processing the volume determined from the measured air flow and the estimated intra-pleural pressure.

This involves obtaining an intra-pleural pressure, which may be generated by the parameter estimator 114 and/or otherwise obtained, plotting lung volume versus intra-pleural pressure, and computing, mathematically, the area within the pressure-volume loop and the chest wall compliance line, which is equal to the work of breathing. Likewise, the information can be provided to the computing system 118 for processing, and/or otherwise utilized.

The physiological parameter determining apparatus 102 can be part of the ventilator 104 and/or other computing device. For example, the apparatus 102 can be part of a computer(s) with a microprocessor(s) that executes a computer readable instruction(s) stored or encoded on computer readable storage medium such as physical memory or other non-transitory medium. Additionally or alternatively, the microprocessor(s) can execute a computer readable instruction carried by a carrier wave, signal or other transitory medium.

FIG. 2 illustrates an example of the physiological parameter determining apparatus 102. The physiological parameter monitoring device 102 includes a lung volume determiner 202, which receives, as an input, the measured air flow and determines a lung volume based thereon. In the illustrated instance, the lung volume determiner 202 integrates the received measured air flow and determines the lung volume based thereon. In other instances, other approaches are utilized to determine the lung volume.

An estimator 204 receives, as an input, the measured air flow, the measured airway pressure, and the determined lung volume. The measured air flow and airway pressure can be conveyed to the physiological parameter determining apparatus 102 as they are determined (i.e., in real-time) or after a predetermined time delay. The estimator 204 employs an algorithm 206 that fits a model 208 to the input measured air flow, the measured airway pressure and the determined lung volume, and determines the intra-pleural pressure based thereon. A non-limiting example of the parameter estimator 114 is described below in connection with FIG. 16.

A Work of Breathing (WOB) determiner 210 receives, as an input, the estimated intra-pleural pressure and the determined lung volume, and determines a WOB value. In one instance, the Work of Breathing (WOB) determiner 210 determines the WOB value based on a WOB algorithm 212, which, in one instance, includes generating a Campbell diagram and computing a WOB, from the non-invasively determined input information, at one or more breathes, including each breath or a sub-set of breaths.

Briefly turning to FIG. 3, an example Campbell diagram 302 is illustrated. A y-axis 304 represents lung volume, which is referenced to functional residual capacity, and an x-axis 306 represents esophageal pressure, which is referenced to a baseline value so that the breaths start at the origin 308 of the diagram (zero pressure and volume point). During spontaneous breathing, the pressure-volume loop 310 moves in a clockwise direction and its slope 312 represents the dynamic lung compliance ($C_L$). During inhalation (I) 314, esophageal pressure decreases and lung volume increases. Exhalation (E) 316 is normally passive, with both volume and pressure returning to zero at the end of the breath.

A line 318, whose slope is equal to the chest wall compliance ($C_{CW}$), is also drawn on the diagram, starting at the zero flow point. With respect to FIGS. 2 and 3, the WOB determiner 210 can determine a WOB as the area enclosed by the inspiratory portion of the non-invasive pressure-volume loop 310 and the chest wall compliance line 318. To determine the slope of the chest wall compliance line 318, the subject can be kept completely relaxed as described in Banner et al., "Partially and totally unloading respiratory muscles based on real-time measurements of work of breathing," *Chest*, vol. 106, no. 6, pp. 1835-1842, December 1994, and/or otherwise. For example, nominal values for $C_{CW}$ can also be used.

With reference to FIGS. 2, 4 and 5, a non-limiting example of the model 208 is discussed. FIGS. 4 and 5 respectively show mechanical and electrical equivalents of an example model 208. In this example, the model 208 represents a first-order single compartment model of the lung with airway pressure ($P_{ao}$), lung resistance ($R_L$), lung compliance ($C_L$) and intra-pleural pressure ($P_{pl}$).

The model 208 can be described, mathematically, as shown in EQUATION 1:

$$P_{ao}(t) = R_L(t)\dot{V}(t) + \frac{1}{C_L(t)}(V(t) - FRC) + P_{pl}(t) + P_0 \quad \text{EQUATION 1}$$

where t represents time, $\dot{V}$ represents air flow into the lungs, V represents lung volume, FRC represents functional residual capacity, and $P_0$ represents a constant term to account for the fact that at FRC, when both the resistive and elastic pressure terms are zero, airway opening pressure $P_{ao}$ is not equal to intra-pleural pressure $P_{pl}$. $R_L$ and $C_L$ are expressed as function of time to indicate that the mechanical properties of the lungs are not constant in time, but rather change throughout the breath.

The last two terms of EQUATION 1 can be combined into a single time-varying term, rendering EQUATION 2:

$$P_{ao}(t) = R_L(t)\dot{V}(t) + \frac{1}{C_L(t)}(V(t) - FRC) + P_0^*(t). \quad \text{EQUATION 2}$$

Rearranging EQUATION 2 in vector form renders EQUATION 3:

$$y(t) \triangleq P_{ao}(t) = \underbrace{\left[R_L(t) \frac{1}{C_L(t)} P_0^*(t)\right]}_{\theta^T(t)} \underbrace{\begin{bmatrix} \dot{V}(t) \\ V(t) - FRC \\ 1 \end{bmatrix}}_{x(t)} \triangleq \theta^T(t)x(t) \quad \text{EQUATION 3}$$

where θ(t) is a parameter vector to be estimated, x(t) is the input vector and y(t) is the output. In EQUATION 3, the output y(t) is the measured airway pressure signal $P_{ao}$, whereas the input is a 3 by 1 vector made of the measured flow signal $\dot{V}$, the volume V above FRC and a constant term equal to 1. The volume above FRC can be obtained by numerical integration of the flow signal.

Using the airway pressure ($P_{ao}$) and the flow ($\dot{V}$) measurements, the parameter vector containing the three different time-varying parameters, $R_L$, $C_L$ and $P_0^*$, can be effectively estimated in real-time using a modified RLS algorithm. An example of a suitable RLS algorithm is discussed in Vahidi, "Recursive least squares with forgetting for online estimation of vehicle mass and road grade: Theory and experiments," Vehicle System Dynamics, vol. 43, no. 1, pp. 31-55, 2005. Other algorithms, RLS and/or non-RLS (e.g., Kalman filter, optimization methods, etc.), are also contemplated herein.

The value of the parameter $P_0^*$ represents, at each time-step, an estimation of the intra-pleural pressure plus an offset term given by the value of the constant $P_0$, as shown in EQUATION 4:

$$P_0^*(t) = P_{pl}(t) + P_0 \quad \text{EQUATION 4:}$$

If the absolute value of intra-pleural pressure is to be estimated, at the end of exhalation ($t=t_{EE}$), when both the resistive and elastic pressure terms in EQUATION 3 are zero, the relationship shown in EQUATION 5 holds:

$$P_{ao}|_{t=t_{EE}} = P_{pl}|_{t=t_{EE}} + P_0 \quad \text{EQUATION 5:}$$

Hence, $P_0$ can be expressed as shown in EQUATION 6:

$$P_0 = P_{ao}|_{t=t_{EE}} - P_{pl}|_{t=t_{EE}} \quad \text{EQUATION 6:}$$

Finally, by plugging EQUATION 6 into EQUATION 4, renders EQUATION 7:

$$P_{pl}(t) - P_{pl}|_{t=t_{EE}} = P_0^*(t) - P_{ao}|_{t=t_{EE}} \quad \text{EQUATION 7:}$$

At each time-step, once the parameter $P_0^*$ is estimated, an estimate of the relative change of intra-pleural pressure with respect to its value at the end of the last exhalation (which is equal to the value at the beginning of the current inhalation cycle) can be obtained in real-time by subtracting the term $P_{ao}$ ($t=t_{EE}$) from $P_0^*$ EQUATION 7. This term can also be obtained in real-time, once per breath, by simply sampling the $P_{ao}$ signal at the end of each exhalation cycle.

The result of the estimation is shown in EQUATION 8:

$$\hat{P}_{pl}(t) = P_{pl}(t) - P_{pl}|_{t=t_{EE}}, \quad \text{EQUATION 8:}$$

The algorithm provides an estimation of the relative change of intra-pleural pressure ($\hat{P}_{pl}$) with respect to its baseline value at the beginning of the current inhalation cycle rather than its absolute value. In constructing the Campbell diagram, the value of intra-pleural pressure can be referenced to its baseline value (i.e., its value at the beginning of the current inhalation cycle) without affecting the computation of the WOB.

FIG. 16 illustrates a non-limiting example in which the parameter estimator 114 employs a recursive least square (RLS) algorithm to estimate the intra-pleural pressure by minimizing a sum of squared residuals between the measured airway pressure and a predicted airway pressure.

A summation block 1602 computes an error between the non-invasively measured airway pressure and a previously estimated airway pressure. The previously estimated airway pressure is estimated based on the lung mechanics model 208, previously estimated lung compliance, lung resistance and intra-pleural pressure parameters, a non-invasively measured air flow, and a derived lung volume.

The estimator 204 determines next estimates of the lung compliance, the lung resistance, and the intra-pleural pressure by minimizing the prediction error. The lung mechanics model 208 then determines a next estimate of an airway pressure based on these estimates. The next estimate of the airway pressure is provided to the summation block 1602, which computes a next error based on these parameters.

The above process of estimating the parameters is repeated. Each estimated intra-pleural pressure is provided to the WOB determiner 210, which uses this information, after acquiring data for a breath, to determine a WOB value in connection with the breath as described herein.

The above describes an approach in which a first-order single compartment model of the lung is fitted to flow and airway pressure measurements, which provides estimated values of intra-pleural pressure, lung resistance, lung compliance, etc. In one instance, the estimation is achieved by minimizing a sum of squared residuals between measured and model predicted airway pressure using a modified recursive least square approach, and the intra-pleural pressure is employed in a Campbell Diagram used to determine a WOB, with non-invasively obtained input, at each breath.

FIGS. 6 and 7 respectively illustrate examples in which the metric determiner 116 and the parameter estimator 114 are omitted. In FIG. 7, a non-invasively determined intra-pleural pressure is provided as an input. The non-invasively determined intra-pleural pressure can be estimated as described herein by another apparatus including the parameter estimator 114 and/or otherwise.

The following provides a non-limiting example of non-invasively determining intra-pleural pressure and a WOB based thereon.

The data are related to a 2-minute window during which the object was subject to Continuous Positive Airway Pressure (CPAP) with Pressure Support Ventilation (PSV). During the 2-minute window the PSV level was reduced from 10 to 0 cmH2O beginning around 350 second.

A non-invasive estimated intra-pleural pressure, estimated as described herein, is shown in the bottom plot of FIG. 8, and a measured esophageal pressure is shown in the top plot of FIG. 8. FIG. 9 shows the estimated lung resistance, and FIG. 10 shows the estimated lung compliance, both estimated as described herein.

In the illustrated example, there is an offset between the non-invasive estimated intra-pleural pressure and the measured esophageal pressure. The offset represents a pressure required to inflate the esophageal balloon. This determines a baseline value of the esophageal pressure ($P_{es}$), which is clearly different from the baseline pressure in the intra-pleural space. Offset correction can be obtained by subtracting a constant term from the esophageal measurements. FIG. 11 shows a corrected esophageal pressure 1102 and the non-invasive estimated intra-pleural pressure 1104.

FIG. 12 illustrates a first pressure-volume loop 1202 of a Campbell diagram created from a corrected measured $P_{es}$ and a second pressure-volume loop 1204 of a Campbell diagram created from an estimated $P_{pl}$. A WOB is determined assuming a known slope of the $C_{cw}$ line 1206.

Low pass filtering the loops 1202 and 1204 may improve agreement between the loops 1202 and 1204 as shown in FIG. 13, where a first filtered pressure-volume loop 1302 created from a corrected measured $P_{es}$ and a second filtered pressure-volume loop 1304 created from an estimated $P_{pl}$ are shown. A WOB is determined, assuming a known slope of the $C_{cw}$ line 1306.

Where the spectral content of respiratory signals and cardiogenic oscillations overlap making it harder to separate the two through low, high or band pass filters, smoothing (averaging) through a time-based window can be used. If the cardiac signal is available from an additional source, such as SpO2 signal, then this signal can be used to cancel out the cardiogenic oscillations from the respiratory signals. The addition of filtering is an enhancement that makes estimates from the proposed technique more accurate.

FIG. 14 illustrates an example method in accordance with the disclosure herein.

It is to be appreciated that the ordering of the acts is not limiting. As such, other orderings are contemplated herein. In addition, one or more acts may be omitted and/or one or more additional acts may be included.

At 1402, a non-invasively measured airway pressure of a subject is obtained.

At 1404, a non-invasively measured air flow is obtained.

At 1406, a lung volume of the subject is determined based on the obtained air flow. As discussed herein, the lung volume can be determined by mathematically integrating the air flow.

At 1408, a prediction error between the measured airway pressure and an estimated airway pressure, which is based on a lung mechanics model and previously estimated parameters, is determined.

At 1410, estimates of lung resistance, lung compliance, and intra-pleural pressure are determined by minimizing the prediction error, as described herein.

At 1412, a new estimate of an airway pressure is determined based on the model, the measured air flow parameter, the determined lung volume parameter, and the estimated lung resistance, lung compliance, and intra-pleural pressure parameters.

Acts 1402-1412 are repeated using the new estimate of the airway pressure.

FIG. 15 illustrates an example method in accordance with the disclosure herein.

It is to be appreciated that the ordering of the acts is not limiting. As such, other orderings are contemplated herein. In addition, one or more acts may be omitted and/or one or more additional acts may be included.

At 1502, a non-invasively estimated intra-pleural pressure of a subject is obtained.

At 1504, a non-invasively measured air flow is obtained.

At 1506, a lung volume of the subject is determined based on the obtained air flow. As discussed herein, the lung volume can be determined by mathematically integrating the air flow.

At 1508, a pressure-volume loop is generated based on the non-invasive estimate of the intra-pleural pressure and the lung volume.

1510, a chest wall compliance line is determined or assumed known.

1512, a work of breathing metric for the subject is determined based on an area within the pressure-volume loop and the chest wall compliance line of the Campbell diagram.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

In FIGS. 1, 2, 6 and 7, the physiological parameter determining apparatus 102 is a stand-alone device. In another example, the physiological parameter monitoring device 102 is part of the ventilator 104, other ventilator (invasive or non-invasive), and/or other device, such as a respiratory support device, with airway pressure and flow signals available as inputs.

The above may provide the following: estimating lung resistance and compliance continuously and in real-time, which will allow sudden changes in the mechanical properties of the lung to be detected; estimating intra-pleural pressure continuously and in real-time without the need of an esophageal catheter, and the estimated waveform can be used to quantify the respiratory muscle workloads by means of WOB, POB or PTP index, and assessing patient's readiness for weaning or extubation.

The above may also provide the following: selecting appropriate pressure support ventilation (PSV) levels so as to avoid excessive respiratory support, resulting in respiratory muscle atrophy, or under-support that can result in respiratory muscle fatigue; introducing a new ventilation mode, where ventilator support is triggered based on the estimated values of intra-pleural pressure, and introducing non-invasive closed-loop control modalities on WOB, POB or PTP index, where the levels of pressure support are automatically adjusted so as to maintain the controlled variables within desired ranges.

The above may be used as a diagnostic or a therapeutic device, where continuous estimates of WOB, lung resistance and lung compliance, plotted as waveforms or trending information can be used to diagnose COPD, ARDS, and other chronic/acute lung diseases, and to guide the related therapy, therapy path and selecting appropriate medical device settings. WOB, computed every breath, real time non-invasive intra-pleural pressure, and lung compliance and resistance can directly be part of any such system, it can also be used as an underlying technique to compute some other clinically significant information.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of estimating work of breathing in a subject receiving mechanical ventilation via a ventilator that includes (a) a sensor to monitor a physiological parameter and (b) a controller, comprising:
    ventilating adapted to provide mechanical ventilation to the subject;
    determining, in the controller, a first physiological parameter indicative of a lung volume of a subject that is based on a second physiological parameter indicative of a non-invasively measured air flow into the lungs of the subject monitored via the sensor;
    obtaining a non-invasively measured airway pressure of the subject;
    obtaining a third physiological parameter indicative of a non-invasively estimated intra-pleural pressure of the subject by non-invasively estimating the intra-pleural pressure of the subject based on the non-invasively measured airway pressure of the subject and the first physiological parameter indicative of the lung volume;
    determining, in the controller, a work of breathing based on the first and third physiological parameters and generating a signal indicative thereof, wherein estimating the intra-pleural pressure is done based on a lung mechanics model, which is a function of the non-invasively measured airway pressure, the air flow into the lungs, the determined lung volume, a lung resistance, a lung compliance, and a predetermined constant; and
    controlling operation of the ventilator to ventilate the subject based on the work of breathing.

2. The method of claim 1, further comprising:
    generating a Campbell diagram based on the first and third physiological parameters; and
    determining the work of breathing based on the Campbell diagram.

3. The method of claim 2, further comprising:
    generating a chest wall compliance line;
    determining an area within a pressure-volume loop of the Campbell diagram and the chest wall compliance line; and
    determining the work of breathing based on the area.

4. The method of claim 1, further comprising:
    determining the work of breathing for each breath.

5. The method of claim 1, further comprising:
    determining the lung volume by integrating the air flow into the lungs.

6. The method of claim 1, further comprising:
    estimating the intra-pleural pressure by fitting the lung mechanics model to the non-invasively measured airway pressure, the air flow into the lungs, the determined lung volume, and the predetermined constant.

7. The method of claim 6, further comprising:
    estimating the lung resistance and the lung compliance by fitting the lung mechanics model to the non-invasively measured airway pressure, the air flow into the lungs, the determined lung volume, and the predetermined constant.

8. The method of claim 7, further comprising:
    estimating the airway pressure based on the lung mechanics model using the estimated intra-pleural pressure, the measured air flow into the lungs, the determined lung volume, the estimated lung resistance, the estimated lung compliance, and the predetermined constant;
    determining a difference between the estimated airway pressure and the measured airway pressure; and
    estimating the intra-pleural pressure by minimizing the difference between the estimated airway pressure and the measured airway pressure.

9. The method of claim 1, further comprising:
    estimating the intra-pleural pressure with $$P_{ao}(t) = R_L(t)\dot{V}(t) + \frac{1}{C_L(t)}(V(t) - FRC) + P_{pl}(t) + P_0$$

where $P_{ao}$ represents the non-invasively measured airway pressure, $R_L$ represents a lung resistance, $\dot{V}$ represents the non-invasively measured air flow, $C_L$ represents a lung compliance, V represents the lung volume, FRC represents a functional residual capacity, $P_{pl}$ represents the intra-pleural pressure, $P_0$ represents a constant term, and t represents time.

10. The method of claim 9, wherein $R_L$ and $C_L$ are time varying parameters.

11. The method of claim 9, further comprising:
    estimating at least one of $R_L$, $C_L$, $P_{pl}$ or $P_0$ in real-time using a recursive least squares algorithm.

12. The method of claim 9, further comprising:
    employing the work of breathing to at least one of assess subject readiness for extubation or select a pressure support ventilation level, diagnose and treat excessive respiratory muscle loading.

13. The method of claim 9, further comprising:
    employing the work of breathing to at least one of diagnose a condition or treat a condition.

14. The method of claim 1, further comprising:
    estimating a relative change of the intra-pleural pressure with respect to a value at an end of a last exhalation.

15. The method of claim 1, further comprising:
    estimating a relative change of the intra-pleural pressure with respect to a value at an end of a last exhalation in real-time by subtracting the non-invasively measured airway pressure from a combination of the estimated intra-pleural pressure and a constant.

16. The method of claim 1, further comprising:
    estimating a relative change of the intra-pleural pressure in real-time by sampling the non-invasively measured airway pressure at an end of each exhalation.

17. The method of claim 1, further comprising:
estimating a relative change of the intra-pleural pressure with respect to a baseline value at a beginning of a current inhalation cycle.

18. The method of claim 1, further comprising:
estimating an absolute value of the intra-pleural pressure at an end of exhalation when both a lung resistance and an elastic pressure are zero.

19. The method of claim 1, further comprising:
obtaining the third physiological parameter with a ventilator;
determining the first physiological parameter with the ventilator; and
determining the work of breathing with the ventilator.

20. The method of claim 1, further comprising:
obtaining the third physiological parameter with a processor of a computer;
determining the first physiological parameter with the processor; and
determining the work of breathing with the processor.

21. A ventilator system for estimating work of breathing in a subject, comprising:
a ventilator to provide mechanical ventilation to the subject;
a work of breathing monitoring system, comprising:
a processor configured to:
determine a first physiological parameter indicative of a lung volume of the subject that is based on a second physiological parameter indicative of a non-invasively measured air flow into lungs of the subject;
obtain a non-invasively measured airway pressure of the subject;
obtain a third physiological parameter indicative of a non-invasively estimated intra-pleural pressure of the subject by non-invasively estimating the intra-pleural pressure by fitting a lung mechanics model to the non-invasively measured airway pressure, the non-invasively measured air flow into the lungs, the lung volume, and a predetermined constant;
determine the work of breathing based on the first and third physiological parameters and generating a signal indicative thereof, wherein estimating the intra-pleural pressure is done based on a lung mechanics model, which is a function of the non-invasively measured airway pressure, the air flow into the lungs, the determined lung volume, a lung resistance, a lung compliance, and a predetermined constant; and
control operation of the ventilator to ventilate the subject based on the work of breathing.

22. The system of claim 21, wherein the processor is further configured to:
generate a Campbell diagram based on the first and third physiological parameters;
generate a chest wall compliance line;
determine an area within a pressure-volume loop of the Campbell diagram and the chest wall compliance line; and
determine the work of breathing based on the area.

* * * * *